(12) United States Patent
Finkielsztein et al.

(10) Patent No.: US 9,867,625 B2
(45) Date of Patent: Jan. 16, 2018

(54) METHODS AND APPARATUS FOR A MANUAL RADIAL ARTERY COMPRESSION DEVICE

(75) Inventors: Sergio Finkielsztein, Newton, MA (US); Marco Finkielsztein, Newton, MA (US)

(73) Assignee: MARINE POLYMER TECHNOLOGIES, INC., Danvers, MA (US)

( * ) Notice: Subject to any disclaimer, the term of this patent is extended or adjusted under 35 U.S.C. 154(b) by 395 days.

(21) Appl. No.: 14/004,314

(22) PCT Filed: Mar. 19, 2012

(86) PCT No.: PCT/US2012/029600
§ 371 (c)(1),
(2), (4) Date: Sep. 25, 2013

(87) PCT Pub. No.: WO2012/129146
PCT Pub. Date: Sep. 27, 2012

(65) Prior Publication Data
US 2014/0012313 A1    Jan. 9, 2014

Related U.S. Application Data

(60) Provisional application No. 61/454,101, filed on Mar. 18, 2011.

(51) Int. Cl.
*A61B 17/135* (2006.01)
*A61B 17/132* (2006.01)
(Continued)

(52) U.S. Cl.
CPC ........ *A61B 17/135* (2013.01); *A61B 17/1325* (2013.01); *A61B 2017/00557* (2013.01); *A61F 5/022* (2013.01)

(58) Field of Classification Search
CPC . A61B 17/135; A61B 17/132; A61B 17/1322; A61B 17/1325; A61B 17/1355; A61B 5/022
See application file for complete search history.

(56) References Cited

U.S. PATENT DOCUMENTS 3,633,567 A * 1/1972 Sarnoff ............. A61B 5/02141
128/DIG. 15
4,041,934 A 8/1977 Genese
(Continued)

FOREIGN PATENT DOCUMENTS

JP    51-053783 A    5/1976
JP    61-217132 A    9/1986
(Continued)

OTHER PUBLICATIONS

Almany et al., Radial artery access for diagnostic and interventional procedures. Radial Artery Access. Accumed Systems, Inc. Ann Arbor, Michigan. 1999: 17 pages.
(Continued)

*Primary Examiner* — Diane Yabut
(74) *Attorney, Agent, or Firm* — Nutter McClennen & Fish LLP

(57) ABSTRACT

A vascular compression apparatus and method for applying pressure onto an area of a patient generally including a blood vessel and a wound site, such as a blood vessel puncture after a cannulated procedure, for the purpose of controlling bleeding and achieving hemostasis.

17 Claims, 7 Drawing Sheets

(51) Int. Cl.
*A61F 5/02* (2006.01)
*A61B 17/00* (2006.01)

(56) References Cited

U.S. PATENT DOCUMENTS

| | | |
|---|---|---|
| 4,307,722 A | 12/1981 | Evans |
| 4,604,762 A | 8/1986 | Robinson |
| 4,633,863 A | 1/1987 | Filips et al. |
| 4,731,073 A | 3/1988 | Robinson |
| 4,760,846 A | 8/1988 | Mers Kelly et al. |
| 4,798,199 A | 1/1989 | Hubbard et al. |
| 4,854,379 A | 8/1989 | Shaubach et al. |
| 5,095,912 A | 3/1992 | Tomita |
| 5,133,734 A | 7/1992 | Lee |
| 5,147,318 A | 9/1992 | Hohn |
| 5,203,337 A | 4/1993 | Feldman |
| 5,263,965 A | 11/1993 | Roth |
| 5,304,201 A | 4/1994 | Rice |
| 5,342,388 A | 8/1994 | Toller |
| 5,492,530 A | 2/1996 | Fischell et al. |
| 5,494,043 A | 2/1996 | O'Sullivan et al. |
| 5,509,423 A | 4/1996 | Bryars |
| 5,554,168 A | 9/1996 | Petersen |
| 5,601,597 A | 2/1997 | Arrowood et al. |
| 5,792,173 A | 8/1998 | Breen et al. |
| 5,876,346 A | 3/1999 | Corso |
| 5,888,247 A | 3/1999 | Benetti |
| 5,947,125 A | 9/1999 | Benetti |
| 5,980,567 A | 11/1999 | Jordan |
| 6,027,521 A | 2/2000 | Ourada |
| 6,068,646 A | 5/2000 | Lam |
| 6,132,417 A | 10/2000 | Kiesz |
| 6,167,889 B1 | 1/2001 | Benetti |
| 6,248,124 B1 | 6/2001 | Pedros et al. |
| 6,332,468 B1 | 12/2001 | Benetti |
| 6,451,257 B1 | 9/2002 | Flamer |
| 6,478,818 B1 | 11/2002 | Taheri |
| 6,514,212 B1 | 2/2003 | Ide et al. |
| 6,589,183 B2 | 7/2003 | Yokozeki |
| 6,644,319 B1 | 11/2003 | Benetti |
| 6,663,653 B2 | 12/2003 | Akerfeldt |
| 6,709,467 B1 | 3/2004 | Kantsevitcha et al. |
| 6,730,040 B2 | 5/2004 | Lee et al. |
| 6,855,162 B2 | 2/2005 | Parodi |
| 6,932,773 B2 | 8/2005 | Inoue et al. |
| 7,498,477 B2 * | 3/2009 | Wada ................ A61B 17/1325 128/100.1 |
| 2001/0044636 A1 | 11/2001 | Pedros et al. |
| 2002/0052552 A1 | 5/2002 | Yokozeki |
| 2003/0009105 A1 | 1/2003 | Lee et al. |
| 2003/0028214 A1 | 2/2003 | Benz et al. |
| 2003/0055453 A1 | 3/2003 | Akerfeldt |
| 2003/0094180 A1 | 5/2003 | Benetti |
| 2003/0114881 A1 * | 6/2003 | Stalemark ............ A61B 17/122 606/201 |
| 2004/0039413 A1 | 2/2004 | Akerfeldt et al. |
| 2004/0260339 A1 | 12/2004 | Pedros et al. |
| 2004/0260392 A1 | 12/2004 | Kantsevitcha et al. |
| 2005/0148886 A1 | 7/2005 | Gong et al. |
| 2006/0229670 A1 * | 10/2006 | Bates ................ A61B 17/0057 606/213 |
| 2007/0016083 A1 | 1/2007 | Hasegawa |
| 2007/0191881 A1 | 8/2007 | Amisar et al. |
| 2007/0233010 A1 | 10/2007 | Perez |
| 2007/0235044 A1 | 10/2007 | Benetti |
| 2008/0097497 A1 | 4/2008 | Assad et al. |
| 2008/0172000 A1 | 7/2008 | Perez |
| 2008/0188863 A1 | 8/2008 | Chu |
| 2009/0281565 A1 | 11/2009 | McNeese |
| 2010/0204553 A1 | 8/2010 | Sonderegger |
| 2010/0210956 A1 | 8/2010 | Im |

FOREIGN PATENT DOCUMENTS

| | | |
|---|---|---|
| JP | 02-109603 U | 9/1990 |
| JP | 06-021608 U | 3/1994 |
| JP | 3136037 U | 10/2007 |
| JP | 3136041 U | 10/2007 |
| JP | 2008-119517 A | 5/2008 |
| JP | 2009-545424 A | 12/2009 |
| JP | 2010-131296 A | 6/2010 |
| WO | 2008/019126 A2 | 2/2008 |
| WO | 2011/090429 A1 | 7/2011 |

OTHER PUBLICATIONS

Rathore et al., A randomized comparison of TR band and radistop hemostatic compression devices after transradial coronary intervention. Catheter Cardiovasc Interv. Nov. 1, 2010;76(5):660-7.
International Preliminary Report on Patentability for Application No. PCT/US2012/029600, dated Oct. 3, 2013 (10 pages).
International Search Report and Written Opinion for Application No. PCT/US2012/029600, dated Oct. 1, 2012 (15 pages).
von Kom et al., A new vascular closure device for the transradial approach: the D Stat Radial system. J Interv Cardiol. Aug. 2008;21(4):337-41.
European Office Action for Application No. 12712188.7, dated Feb. 23, 2016 (6 pages).
Japanese Office Action for Application No. 2013-558229, dated Jan. 12, 2016 (5 pages).

* cited by examiner

METHODS AND APPARATUS FOR A MANUAL RADIAL ARTERY COMPRESSION DEVICE

CROSS REFERENCE TO RELATED APPLICATIONS

The present application is a '371 U.S. national phase application of PCT/US2012/029600, filed Mar. 19, 2012, entitled "Methods and Apparatus for a Manual Radial Artery Compression Device." which claims priority to U.S. Provisional Application No. 61/454,101 filed Mar. 18, 2011, entitled "Methods and Apparatus for a Manual Radial Artery Compression Device," each application of which is hereby incorporated by reference in its entirety.

FIELD OF THE INVENTION

The present disclosure relates to a radial artery compression device. In particular, this invention relates to a self-contained manual vascular compression device and a method for controlling bleeding and facilitating closure of the radial artery. More specifically, the present disclosure relates to a radial artery compression device configured to be releasably secured to the wrist of a patient and to provide an adjustable level of compression pressure on the radial artery to achieve hemostasis at, or in the area of, a vascular access site.

BACKGROUND OF THE INVENTION

Current estimates put the number of cardiac catheritization procedures and interventions at over three million per year. Historically, such procedures were performed via the femoral artery. Since 1989, however, the number of cardiac procedures performed through the radial artery has increased significantly. The benefit of radial access lies in the potentially lower direct costs, patient preference, lower incidence of vascular complications (and their subsequent costs), as well as earlier ambulation. patients, the radial artery branches off of the brachial artery just below the level of the elbow crease. At this point, it passes on the lateral margin of the forearm until it reaches the level of the wrist. There are a significant number of patients (reported to be up to 12%) that may have an anatomic variant. The most common involves the radial artery originating just superior to the elbow, although in a few patients it may originate much higher in the arm.

In a typical cardiac intervention procedure through the radial artery, a sheath having a haemostatic valve is utilized to access a peripheral artery utilizing the administration of a local anesthetic at the vascular access site. A pre-shaped catheter is then introduced into the patient's vasculature through the sheath. The catheter can then be advanced to the ostium of the relevant coronary artery or to another desired location within the patient. The catheter enables delivery of medical instruments, medicines or fluids such as radiography contrast medium, angioplasty wires, balloons, and stents. During or after completion of the procedure, the sheath and catheter are removed and hemostasis can be achieved by manual compression, suturing the access site, or by utilizing another direct repair procedure.

The relatively superficial position of the distal radial artery enables relatively direct application of compression to the artery to achieve and maintain hemostasis during a procedure. Additionally the radial artery allows quick and direct closure at the catheter access site as soon as the arterial catheter has been removed at the end of the procedure.

As with any arterial puncture, achieving hemostasis during and/or after a procedure can be challenging. Typically the access site, or opening, in the artery is created utilizing a micropuncture apparatus, dilator or can even be formed utilizing a single straight incision to form a slit in the artery. The arterial walls include a layer of smooth muscle cells that expand and contract in conjunction with the rhythm of the heart to complement the pumping of the heart and to facilitate movement of blood throughout the body. The expanding and contracting of the radial artery may present challenges to achieving hemostasis at the access site. As a result of this and other factors, during the course of the procedure, blood may leak through the access site and around the outside diameter of the sheath or catheter. Existing radial artery compression devices are not adapted to provide desired and/or adjustable compression to the radial artery at the vascular access site during the course of a procedure.

When the procedure has been completed, typically the catheter is removed and the practitioner or medical professional will apply pressure at the vascular access site to achieve hemostasis and effectuate closure of the vascular access site. One technique for achieving hemostasis is to apply pressure at, or at a point slightly upstream, of the vascular access site. Typically, continuous pressure is necessary to stop bleeding and achieve hemostasis at the access site. While the applied pressure should remain relatively constant, there are advantages to applying a higher level of compression pressure at the beginning of the compression period and then reducing the level of compression pressure after a determined amount of time has elapsed. By gradually reducing the compression pressurization during the compression period, while continually maintaining at least a threshold level of compression, blood can begin to flow through the artery at a reduced pressure, providing nutrient rich blood to the tissue downstream from the access site. Blood flowing through the artery can then hasten clotting to enable hemostasis without application of ongoing compression. Not only can this provide improved closure, but also can improve the relative comfort of the patient.

Compression is typically applied to an access site by a nurse or other practitioner by manually holding a dressing at the access site. Although employing a practitioner to provide compression permits the gradual reduction of pressurization at the access site, it can also be a costly use of practitioner time. Alternative existing radial artery compression techniques which do not require the ongoing manual application of pressure by the practitioner may employ tape or a compression bandage at the vascular access site. These devices and techniques, while allowing the practitioner to attend to other matters, can render it difficult or impractical to adjust the compression pressure while maintaining continuous pressure. As a result, the tape or compression bandages may end up being positioned around the access site without being loosened or adjusted until they are removed.

Various types of automated manual solutions have been developed to, in part, address these issues. One example of an automated solution is shown by Petersen in U.S. Pat. No. 5,554,168. Petersen describes a free standing apparatus which may be attached to the bottom frame of a hospital bed. A pressure applying head is mounted on a swing arm attached to the vertical shaft of the base and can be positioned directly above the wound. Pressure is developed by either compressed air or an electric motor. Two pressure shoes can be positioned to provide both vertical and horizontal pressure.

Another automated solution is described by Lee in U.S. Pat. No. 5,133,734. Lee discloses a pneumatically operated femoral artery compressor applying calibrated and calibrateable external pressure on the puncture site of the femoral artery with the plunger end of a mounted pressurized assembly.

Breen et. al describes another type of partly automated solution, which also uses pneumatic pressure, in U.S. Pat. No. 5,792,173. Breen describes a wound closure device that includes an inflatable balloon with an inflation and deflation outlet. The balloon is coupled to patch, having an aperture for receiving the inflation/deflation outlet. The assembly is coupled to the placement patch and is held via a belt strap at either the wound site or on a bleeding vessel.

McNeese et al (US Pub. No. 2009/0281565) describes an even more complicated solution comprising a rotatable knob coupled to a threaded shaft and a pad. The screw can be tightened to provide pressure on the radial artery.

These automated compression devices are far from ideal, however. They tend to be expensive, difficult to maintain in good working order, consume a great deal of space and are difficult to keep sterile.

A number of manual compression devices have been described as well. Roth, in U.S. Pat. No. 5,263,965, describes a device that is used to apply direct pressure to arterial and venous incisions to promote hemostasis. It consists of a round flat disk with a user manipulable member used for applying downward pressure. In the preferred embodiment of the invention, the user manipulable member consists of a peg over which a cylindrical weight is pivotally mounted. A stretchable bandage is used to secure the weight in place.

Another type of manual compression device is described by Toller in U.S. Pat. No. 5,342,388. This manual compression aid is comprised of a cylindrically shaped handle above a sterile disposable disk. The disk is placed above the catheter insertion point with the catheter inside the notch of the disk. As the catheter is removed, pressure is applied to the handle to force the disk to compress the artery and thereby control bleeding—ultimately achieving hemostasis. This type of device has a number of disadvantages including: the cost of the apparatus; the difficulty associated in ensuring a minimal level of cleanliness; and the time associated in connecting the disposable disk to the assembly prior to its use on a patient.

Benz et. al describe another form of manual compression device in Pub No. US 2003/0028214. This manual vascular compression device also includes a handle an elongated shaft and a pad or disk. In this device the pad or disk is integral to the assembly and the entire apparatus is disposable. Like the pad of Toiler, the pad is flat and contains a notched or equivalent area for locating the catheter.

These, as well as currently commercially available hemostatic control devices such as the Radistop (RADI, Uppsala, Sweden), and the TR Band (Terumo, Japan) have been moderately effective in helping to achieve hemostasis in radial artery interventions and have established the standard of care at between 2-6 hours post-procedure to achieve hemostasis, as well as having significant potential for re-bleeding. These relatively long latencies in achieving result in increased patient discomfort as well significant healthcare (e.g., nursing and monitoring) resources being devoted to patients. What is therefore needed is a more efficient system for achieving radial artery hemostasis more quickly and efficiently and with a reduced potential for re-bleeding.

SUMMARY OF THE INVENTION

The present invention relates to a radial artery compression system.

In a first aspect, the radial artery compression system is comprised of a radial artery compression device. The radial artery compression device of the invention is configured to be releasably secured by a strap or band to the underside of a wrist of a patient to provide continuous and adjustable compression in the area of a radial artery access site. The radial artery access site can be an opening formed utilizing a micropuncture apparatus, a dilator, an incision, or other percutaneous access device or procedure which allows insertion of a sheath and/or a catheter into the radial artery. The radial artery compression device can be configured to provide compression pressure in the area of the radial artery access site to achieve hemostasis. The radial artery compression device of the present invention is effective for achieving hemostasis at the access site during and after a medical procedure such as a vascular delivery procedure.

According to one embodiment, the radial artery compression device includes a body having a pump, a pressure control device and a pressure bladder. As the pump is engaged the pressure bladder is filled with fluid, and the pressure bladder applies pressure through the skin of a subject onto the radial artery. In one embodiment, the pump comprises a fluid containing bladder, which when depressed or otherwise compressed moves fluid from the pump to the pressure bladder, thereby increasing the pressure on the radial artery. Ina preferred embodiment the fluid is air. The pressure control device regulates the pressure in the pressure bladder. In one embodiment, the pressure control device can be actuated to release fluid from the pressure bladder thereby reducing the pressure in the pressure bladder. In another embodiment, the pressure control device is bidirectional and serves to allow fluid, preferably air, into the pump, which the pump then transmits to the pressure bladder. In a preferred embodiment, the pressure control device is a valve. In a most preferred embodiment the pump and the pressure bladder are formed as a unitary piece. In another aspect the pump, the pressure bladder and the pressure control device are disposed on a single plane and form a unit. In a most preferred embodiment the body of the radial artery compression device which comprises the pump, the pressure bladder and the pressure control device is such that the entire unit may be disposed on a patient's arm or wrist and no portion of the device extends past the boundaries of the patients limb.

The radial artery compression device can further comprise a band coupled to the body and configured to secure the body to the underside of a wrist of a patient in the area of the radial artery.

The radial artery compression device can further comprise a covering or sheathing that covers and/or encloses portions of the pump and the pressure bladder. In one embodiment, the covering is disposed on at least a portion of the top surface of the pressure bladder (i.e. the surface not in contact with the patient) and serves to restrain the pressure bladder from expanding thereby directing the force of the pressure bladder in the direction of the radial artery.

In a further embodiment the radial artery compression system comprises (a) the radial artery compression device including the various embodiments described above; and (b) a brace for immobilizing the wrist of the arm to which the radial artery compression device is attached. In one aspect, the brace is comprised of (a) an elongated rigid member having a proximal and distal end; and (b) a plurality of fasting members disposed at the proximal and distal ends of said member and capable of securing said elongated rigid member to the wearer's forearm. In one preferred embodiment, the rigid member is curved throughout its length and about its longitudinal axis. The brace is positionable on the dorsal aspect of the forearm wrist and hand to support and immobilize the portion of the hand proximal to the wrist, the wrist and the portion of the forearm proximal to the wrist and among other functions prevents rotational movement of the hand around the wrist joint.

In a further embodiment the radial artery compression system of the invention comprises (a) the radial artery compression device including the various embodiments described above; optionally (b) a brace for immobilizing the wrist of the arm to which the radial artery compression device is attached; and (c) a compression pad disposed to be in direct contact with the wound site. In one aspect the compression pad is comprised of a hemostatic agent. In a preferred embodiment the hemostatic agent is poly-N-Acetyl Glucosamine.

The invention also contemplates a method for compressing a radial artery at an access site of a radial artery of a subject, the method comprising: (a) providing a radial artery compression device comprising, a pump to be actuated by a user by application of pressure to said pump, a pressure bladder capable by being inflated by the pump and pressure regulation means for regulating the pressure exerted by the pressure bladder; (b) positioning the device such that the pressure bladder is in contact with the underside of the patient's wrist near an access site, the access site providing access to the radial artery; (c) attaching the device to the wrist of a patient, with the pressure bladder; and (d) manually actuating the pump and inflating the pressure bladder to a desired pressure.

In one aspect of the method the invention, the method further comprises providing a brace, as disclosed above, configured to secure the patient's wrist from rotating or moving; affixing the brace to the dorsal (back) side of patient's wrist.

In yet another aspect of the method of the invention, the method further comprises providing a compression pad to be disposed between the pressure bladder of the compression device of the invention and the underside of the patient's wrist.

In one embodiment the method of the invention further comprises a device being inserted into the radial artery via the access site. In a preferred embodiment the pressure provided by the pressure bladder is sufficient to cause hemostasis.

In a preferred aspect of the invention, the use of the system of the invention will result in hemostasis in one hour or less, preferably in 30 minutes or less and most preferably in 15 minutes or less. In one aspect hemostasis may be achieves within 10 minutes.

In another preferred aspect, the incidence of any complication associated with use of the system is less than 10%, preferably less than 5% and most preferably less than 1%.

DETAILED DESCRIPTION OF THE INVENTION

Figure 1:
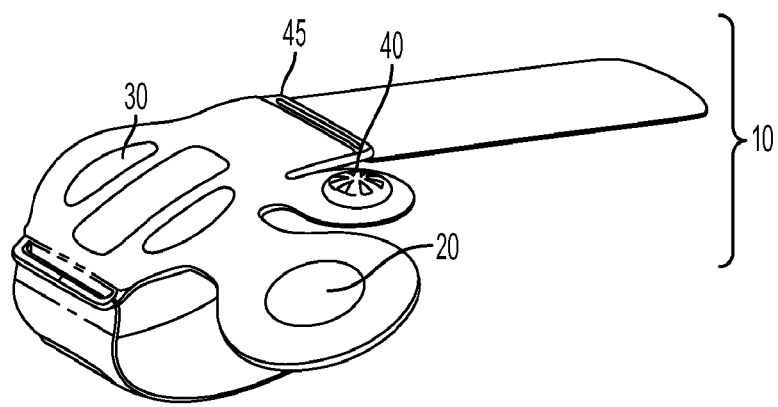
FIG. 1 is a front perspective view of the radial artery compression device of the invention.

To more clearly set forth the invention, reference will be made to the embodiments illustrated in the drawings and specific language will be used. Nevertheless, it should be understood that the invention should not be deemed limited to particular embodiments, descriptions or drawings contained herein.

The vascular compression apparatus of the invention is used on a patient to apply pressure on an area near or at a wound site, such as a blood vessel puncture, most often after a cannulated procedure such as angioplasty, for the purpose of controlling the patient's bleeding and, further, of achieving hemostasis. Specifically, the device may be used to provide pressure and control hemostasis of the radial artery.

FIG. 1 shows the manual vascular compression device of the invention 1. The device has a body 10 having pump 20, a pressure bladder 30 and a pressure control mechanism 40. The pump is in direct fluid connection with the pressure bladder 30. In turn, the pressure bladder 30 is in direct fluid communication with the pressure control mechanism 40. As shown in FIG. 1 the pressure control mechanism 40 and the pump 20 are not in direct fluid communication with each other and are otherwise only connected through the pressure bladder 30.

The pressure bladder 30 may take a number of different forms but is generally made out of any flexible and/or pliable material. The device is placed on a patient's body on or near the area that requires hemostasis or occlusion. The bladder is inflated by means of the pump 20 using a fluid. Preferable the fluid is a gaseous fluid, most preferably the fluid is air.

It is preferable that the pressure bladder be inflated to a volume sufficient to provide hemostasis and/or occlude the vessel of interest, without occluding other vessels. This is particularly important in the case of cardiac interventions through the radial artery. In a preferred embodiment the pressure bladder is capable of being inflated with about 15-25 cc of fluid and in a preferred embodiment the pressure bladder is capable of inflated to a volume of no more than about 20 cc.

The device of FIG. 1 also includes securing means 50 for securing the body to a patient's body, for use in providing pressure for hemostasis. Preferably the device 1 is secured to a patient's for aid in providing pressure to the radial artery. The securing means may be a unitary piece or may be two separate pieces akin to a watch band.

Figure 2:
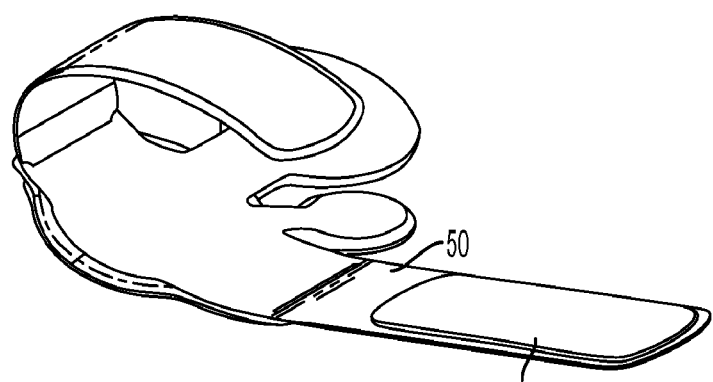
FIG. 2 is a rear perspective view of the radial artery compression device of the invention shown in FIG. 1.

FIG. 2 is a rear prospective view of an embodiment of the subject device and shows further details of the securing means including optional attachment means 90 that can be disposed on the securing means 50 to secure the device 1 to the patient. In one embodiment the attachment means may be a portion of hook and loop fastener such as VELCRO®. Alternatively the securing means may comprise adhesives including adhesive table or a system of holes and tines similar to a conventional watch band.

Figure 3:
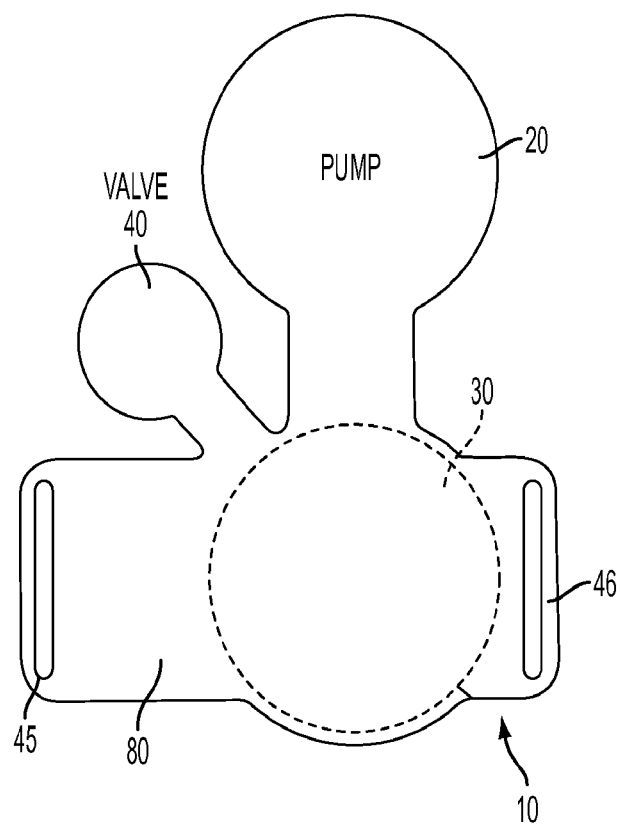
FIG. 3 is a top view schematic of the central portion of the radial artery compression device of the invention shown in FIG. 1.
Figure 4:
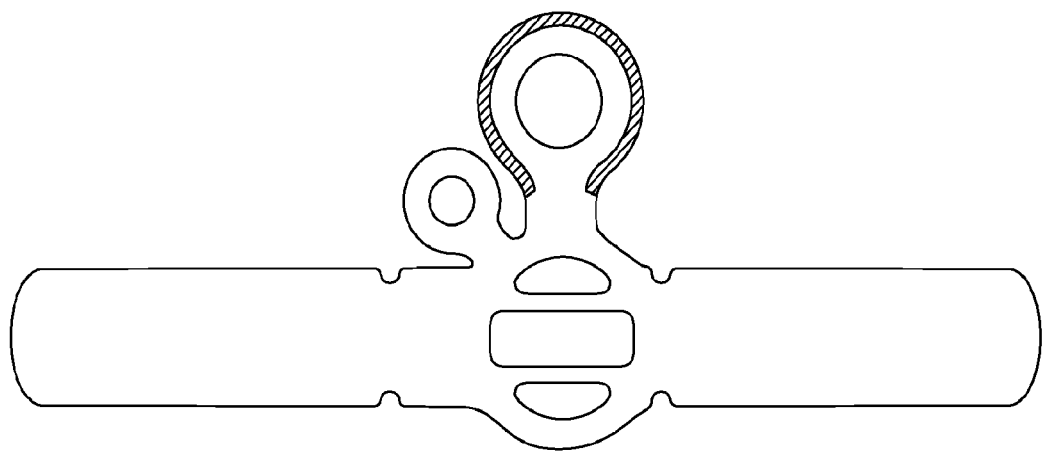
FIG. 4 is a top view of the radial artery compression device of the invention shown in FIG. 1.

FIG. 3 is a schematic of the device body 10 and further shows the relationships of the various components to one another. FIG. 3 further shows optional coupling means for coupling device body 10 to the securing means 50. In the illustrative embodiment the coupling means comprises openings 45 and 46 in the device body which allow the securing means 50, which is preferably a flexible band to pass, through and secure and couple the securing means 50 to the device body. In a preferred embodiment the securing means is unitary in nature (i.e. a single continues piece) and is disposed through the openings 45 and 46 and over the device body 10. FIG. 4 is a schematic of just such a securing means.

Figure 5:
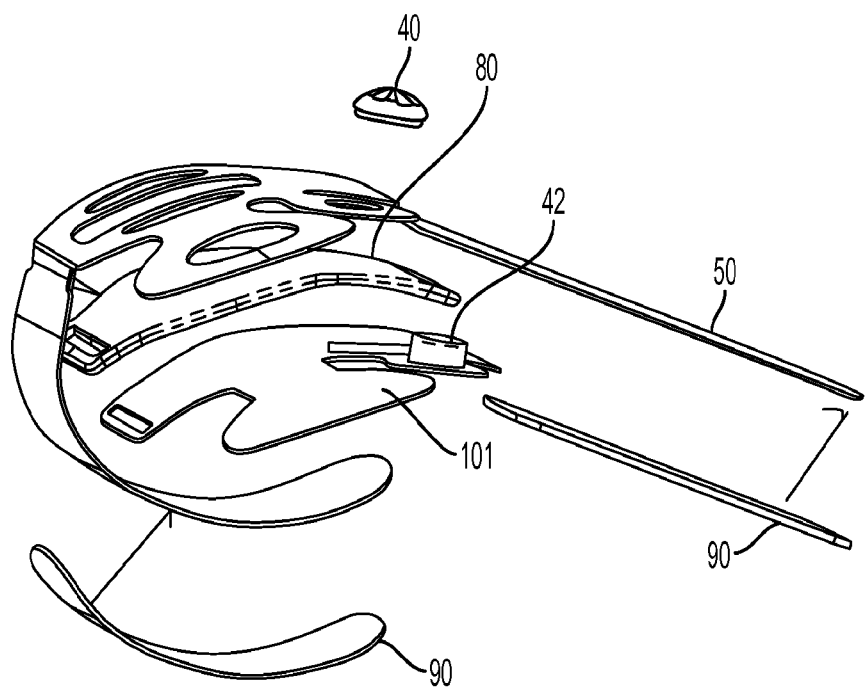
FIG. 5 is a partially exploded perspective view of the radial artery compression device shown in FIG. 1.

FIG. 5 shows a partial exploded view of the embodiment of FIG. 1. The view shows an optional restrictor 80, which is disposes between the device body 10 and the securing means 50. The restrictor is made of a rigid or semi-rigid material and serves to focus the force of the expanding pressure in a downward direction towards the patient. FIG. 5 also shows one embodiment of the pressure regulator 40 comprising a valve 41 and a valve receptacle 42, the valve receptacle being integral to the device body.

In one embodiment, the pump 20 is a commercially available configuration which has been refined for efficient actuation between the thumb and side of pointer finger. The pump may optionally include an integral check valve to allow flow into the bladder and a return element to restore the pump to the starting position. The return element may take a number of different form including a spring, elastic or other type of device that is capable of providing sufficient force to return the pump to its starting position including but not limited to spring(s), elastics or other devices. In one embodiment the return element is made of foam, and provides a force to the pump when the pump is compressed.

In one aspect, where the fluid used to operate the device is air, a hole or other opening in the surface of the pump is introduced to allow the pump to refill with air on the return stroke. In a preferred embodiment, the hole is closed by the thumb during pumping to create pressure and hence flow through the check valve into the bladder.

The bladder 30 is a generally spherical inflatable chamber which applies pressure between the bridge and the patient's wrist. The size of the bladder was developed to allow sufficient stroke to fill the space under the bridge and transfer the internal pressure to the patient incision site. The spherical form allows focusing the applied force at the point of contact at the center of the footprint. The pressure capacity, volume, and reliability requirements of the bladder have not been determined.

The pressure control mechanism 40 can take a number of different forms. As discussed above, in one aspect, the pressure control mechanism 40 is comprised of a valve 41 for exhausting the fluid and a valve receptacle 42. In one embodiment, the exhaust valve is a normally closed valve seated by a spring and the closure force is increased when the bladder is pressurized. When actuated via pressing a button on the valve, the valve opens allowing flow which exhausts the pressure in the bladder.

In one aspect of the invention the pressure bladder 30 is connected to the pressure control mechanism 40 through an exhaust path. The exhaust path may optionally contain a flow restrictor in the channel between the bladder and the exhaust valve. The flow restrictor may be used to control the exhaust flow rate so the user can reduce the pressure in a gradual and controlled manner. In a preferred embodiment, the flow restrictor is 0.006" in internal diameter and 0.25" long.

The vascular compression device is generally molded of a mostly flexible material. The only requirement is that the material is sturdy enough to withstand the application of downward pressure onto a human patient, sufficient to cause a complete occlusion of an artery. Generally, the device should be capable of promoting hemostasis at blood pressure of at least about 200 mm or mercury or 3.9 PSI. In a preferred embodiment, the device should be capable of generating at least about 8 PSI or greater of internal pressure or in other words at least about 2 times the blood pressure. The device 1 may be packaged and sterilized as a sterile medical product so that the user needs not clean or wash it prior to its use. In a preferred embodiment the material is transparent so that the user can more easily align the device with the wound.

In a further embodiment, the radial artery compression system of the invention comprises: (a) the radial artery compression device defined herein in all of its aspects and embodiments; and (b) a brace for restricting the movement and/or rotation of the subject's wrist. Applicants have found that restricting movement of the wrist and associated structures improves the performance of the system and ultimately improves patient outcomes.

Figure 6:
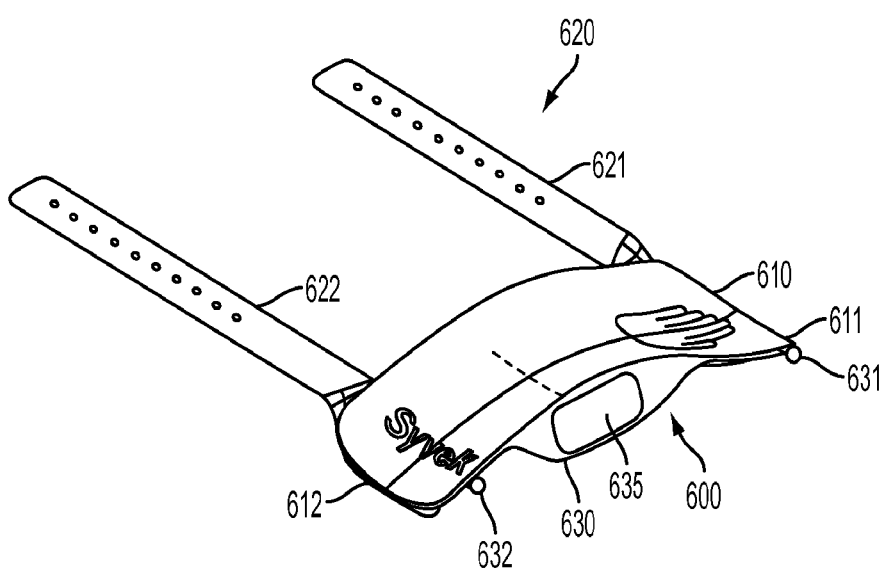
FIG. 6 is a perspective view of an exemplar brace of the invention.

FIG. 6 shows an exemplar embodiment of the brace of the invention In this embodiment the brace 600 has a an elongated rigid member 610 having a proximal end 612 and distal end 611 along which a subject's forearm and hand would be disposed in a "palm up" orientation; the palm being disposed across and along the distal end 611. The brace also has a plurality of fastening members 620 to secure the brace to the subject's arm. In the pictured embodiment, at least one fastening member 631 attaches to a fastener 611 at the distal end of the brace, thereby securing the subject's hand and a second fastening member 622 attaches to a fastener 632, thereby securing the subject's forearm. In the pictured embodiment the fastening member 620 are permanently attached on one side of the brace and are fastened to the fasteners 631 and 632 on the opposite side of the brace. One of ordinary skill, however would realize that the brace could be attached using a plurality of fastening members in other ways.

In the illustrated embodiment the brace includes one or more side-walls 630 that are disposed approximately perpendicularly to the elongated rigid member 610 of the brace. The optional side walls provide for better placement of the brace as well as further enhance the ability of the brace to restrict movement of the wrist and its associated structures. The side wall of the brace may also have a securing region 635 to which the securing means 50 of the vascular compression device 1 may be secured. In one embodiment the securing means may be a hook and loop type of fastener such as VELCRO.

Figure 7A:
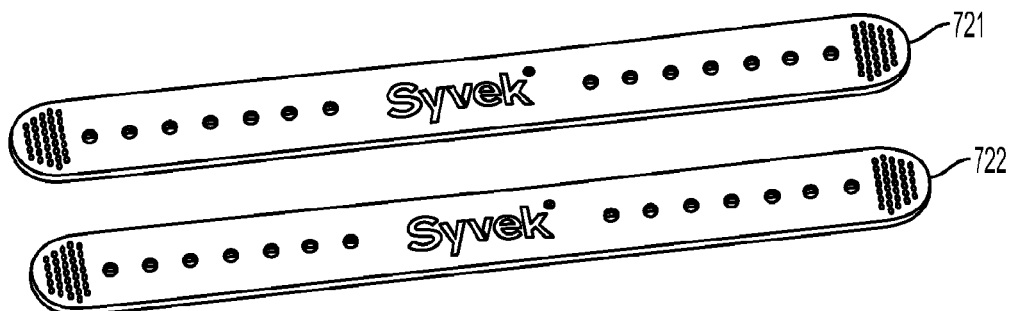
FIG. 7A is a top perspective view of the exemplar brace of the invention.
Figure 7B:
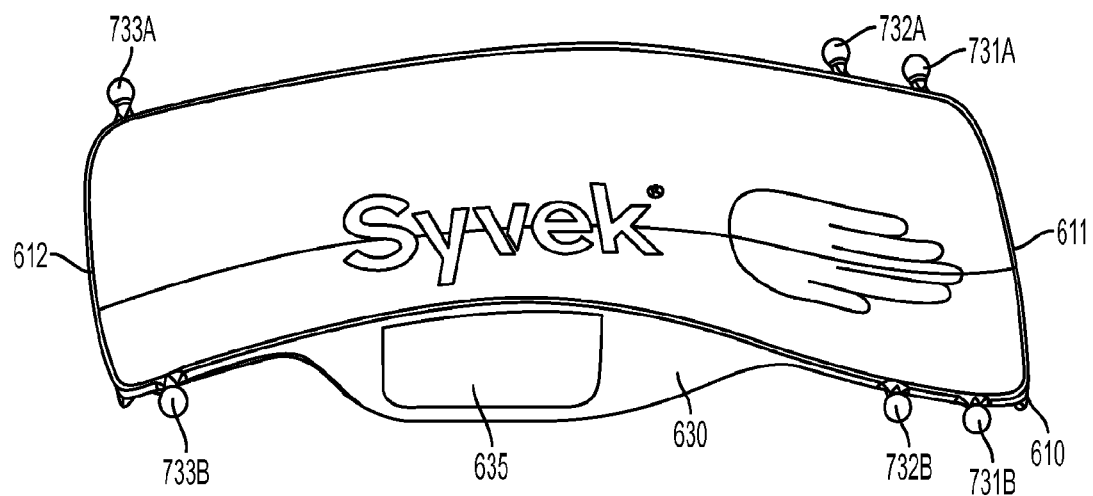
FIG. 7B is a top view of the elongated rigid member of an exemplar brace of the invention.

In one preferred embodiment, the rigid member is curved throughout its length and about its longitudinal axis. The brace is attached on the dorsal aspect of the forearm, wrist and hand to support and immobilize the portion of the hand proximal to the wrist, the wrist and the portion of the forearm proximal to the wrist and among other functions prevents rotational movement of the hand around the wrist joint. FIGS. 7A and 7B show an alternative fastening arrangement of the brace 610. FIG. 7A shows a pair of fastening members 721 and 722 that are detachable from the brace and can be fastened at various positions through a series of holes. FIG. 7B shows the brace 610 having a plurality of fastener pairs (731A and 731B) and (732A and 732B) disposed at the distal end 611 of the brace 610 to which a fastener 721 may be attached. A second fastener 722 would be attached to a second pair 733A and 733B of fasteners at the proximal end 612 of the brace 610.

Figure 8A:
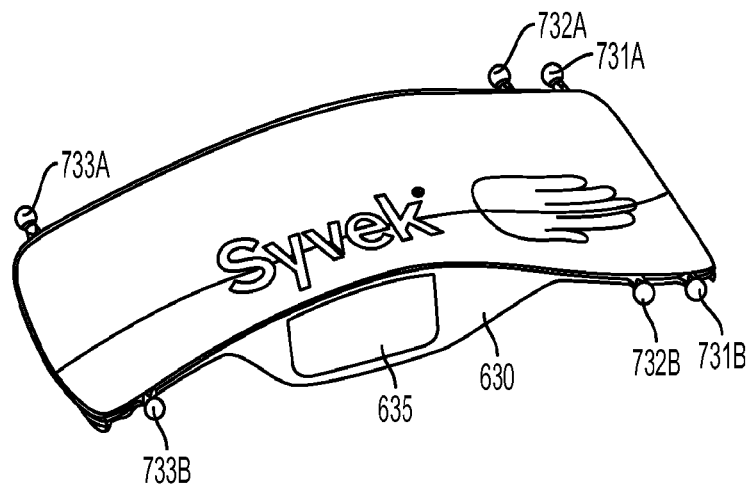
FIGS. 8A and 8B are a top view and a bottom view respectively of the elongated rigid member of an exemplar brace of the invention.
Figure 8B:
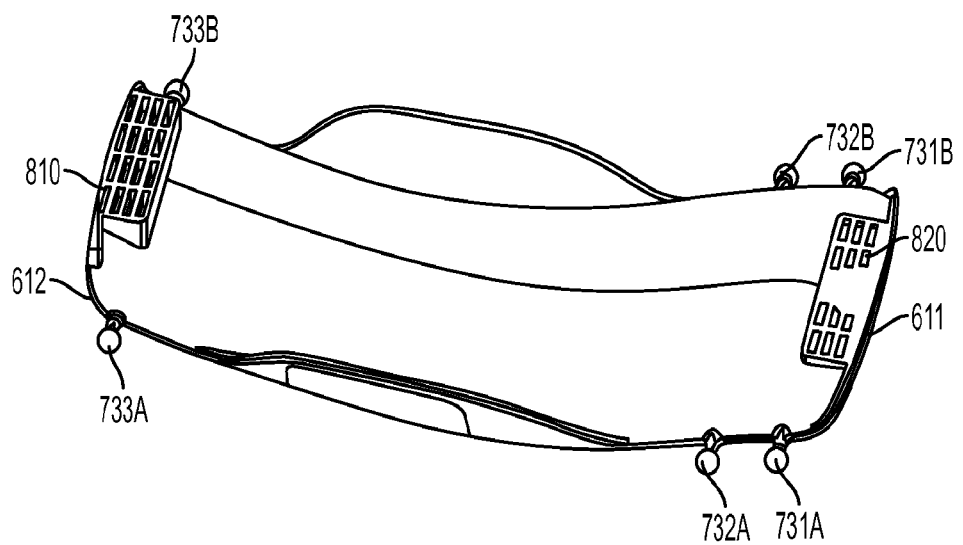

FIG. 8 shows the embodiment of FIGS. 7A and 7B with the addition of a plurality of moldable flat areas 810 and 820. These moldable flat areas, which may be incorporated in any embodiment of the invention provide for a location to which adhesive may be applied to better secure the brace to the dorsal side of the forearm. IN one embodiment the adhesive may be a double-sided adhesive tape, but any suitable adhesive would be appropriate.

This detailed description of the invention is for illustrative purposes only. A reading by those skilled in the art will bring to mind various changes without departing from the spirit and scope of the invention.

EXAMPLES

Prior Art Devices

The standard of post procedure care for achieving hemostasis following radial artery diagnostic and interventional cardiac catheterization is typically 2 to 6 hours, using a variety of compression techniques.

An analysis of the current standard of care of the two most used devices the TR Band which is a wrist band based compression device and the Radistop which is an immobilization based device produced the following results (Comparison of TR Band ad Radistop Hemostatic Compression Devices After Transradial Coronary Intervention, *Catheterization and Cardiovascular Interventions* 76:660-667 (2010))

Wrist Band (TR Band, Terumo, Japan)
Time to Hemostasis: 5.3±2.3 hours
Lowest Time to Hemostasis: 1 hour obtained in approximately 3% of the patients
Local Complication
Ecchymosis 11.4%
Oozing 6.1%
Large hematoma 2.8%
Small hematoma 6.1%
Arm Immobilization (Radistop, RADI, Uppsala, Sweden)
Time to Hemostasis: 4.8±2.2 hours
Lowest Time to Hemostasis: 2 hours obtained in approximately 10% of the patients
Local Complication
Ecchymosis 10.6%
Oozing 7.1%
Large hematoma 1.5%
Small hematoma 4.8%

The addition of a hemostatic patch also does not seem to greatly improve results. A recent study (Korn et al., *A New Vascular Closure Device for the Transradial Approach*, Journal of Interventional Cardiology Vol. 21, No. 4, 2008) Showed the following results:
Wrist Band with Thrombin Hemostatic Patch
Mean duration of compression 4.6 hours
Bleeding after removal of the system 18.6%
Hematoma >5 cm 4.4%
Other complications (paresthesia of the thumb) 0.9%
It appears from the literature that regardless of the system used the mean time to achieve hemostasis is approximately four hours. And that the lowest reported hemostasis time was obtained by Rathere et al at 1 hour. This was obtained in only 3% of the patients receiving an arm immobilization device.

Methods:

Based on these results a clinical trial was organized to test if the subject invention could increase the proportion of patients achieving hemostasis in one hour.

Fifty (50) patients undergoing diagnostic and interventional radial cardiac catheterization were studied as follows:

Group A

In 15 patients hemostasis was attempted using application the wrist band component of the invention plus Syvek Patch. The Syvek patch is a hemostatic patch comprising poly-N-Acetyl-Glucosamine (p-GlcNAc) as the hemostatic agent. The 15 patients were randomly assigned to 10, 30, or 60 minute compression intervals and hemostasis was assessed at each of these intervals. Hemostasis is defined as the ceasing of bleeding with no re-bleeding within 1 hour of the initial hemostasis.

Group B

In 35 patients hemostasis was attempted using the invention (wrist band and the brace) plus a Syvek Patch. The 35 patients were randomly assigned to 10, 30, or 60 minute compression.

Plethysmography and oxymetry were recorded and a Barbeau classification was determined for both radial and ulnar artery flow at baseline, immediately after compression release, and 1 hr, 4 hr, and 1 day post hemostasis depending on the length of patient hospital stay.

Results:

Group A 15 patients hemostasis was attempted using the wrist band component of the invention plus Syvek Patch (p-GlcNAc): Hemostasis was successful as follows:
10 minutes—3 successful, 2 failures
30 minutes—4 successful, 1 failure
60 minutes—5 successful, 0 failures
No local complications Group B 35 patients hemostasis was achieved using the invention (wrist band and the brace) plus a SyvekPatch.
Hemostasis was successful as follows:
10 minutes—12 successful (92.3%), 1 failure
30 minutes—12 successful (100%), 0 failures
60 minutes—10 successful (100%), 0 failures
No local complications Results:

Unexpectedly the subject invention not only increases the proportion of patients achieving hemostasis at one hour from 3% to 100% but also was able to achieving hemostasis at 30 minutes (100%) and at 10 minutes (92.3%). Remarkably, the patients treated with subject inventions had no local complications.

What is claimed is:

1. A radial artery compression system comprising a radial artery compression device, the radial artery compression device adapted to allow a user to provide varying degrees of pressurization against a patient's radial artery to maintain a desired degree of hemostasis at a percutaneous access site, the radial artery compression device comprising:
   a body, the body comprising:
      a pump having a check valve,
      a pressure bladder, and
      a pressure control mechanism that can be activated to release fluid from the pressure bladder, thereby reducing a pressure in the pressure bladder, wherein the pump, the pressure bladder and the pressure control mechanism are disposed on a single plane and form a unit, and securing means to secure the body to the underside of a wrist of a patient in the area of the radial artery, such that the pressure bladder can be positioned adjacent the wrist of the patient;

wherein the user activates the pump to inflate the pressure bladder between a first position and at least a second position to provide varying degrees of pressurization to the wrist of a patient in a manner that prevents blood from flowing out through an opening in the patient's radial artery to thereby achieve hemostasis at the access site;

wherein when the pressure bladder is in the first position, the pressure bladder applies a first amount of pressurization against the wrist of the patient and when the pressure bladder is inflated to the second position by actuation of the pump, the pressure bladder provides a second greater amount of pressurization against the patient's wrist than the first amount, and when the pressure bladder is deflated to a third position by activation of the pressure control mechanism, the pressure bladder provides a third amount of pressurization against the patient's wrist that is greater than the first amount of pressurization and less than the second amount of pressurization.

2. The radial artery compression system of claim 1 further comprising a brace, the brace being adapted to restrict movement of the wrist.

3. The radial artery compression system as in claim 1 further comprising a compression pad comprised of a hemostatic agent.

4. The radial artery compression system according to claim 3 wherein the hemostatic agent is Poly-N-Acetyl-Glucosamine.

5. The radial artery compression system according to claim 1, Wherein the pressure bladder is in continuous fluid communication with the pump.

6. The radial artery compression system as in claim 1, wherein the pressure bladder is in direct fluid communication with the pressure control mechanism, and the pressure control mechanism, pressure bladder and pump all form a unitary component.

7. The radial artery compression device of claim 6, wherein the check valve is integral to the pump.

8. The radial artery compression device of claim 6, further comprising a channel between the pressure bladder and the pressure control mechanism.

9. The radial artery compression device of claim 8, further comprising a flow restrictor disposed in the channel.

10. The radial artery compression system of claim 1, wherein the securing means is a single unitary piece.

11. The radial artery compression device of claim 1, wherein when the device is secured to the underside of the wrist of a patient, as the pressure bladder is inflated to cause a compression pad to exert a force toward the wrist and radial artery of the patient, the pressure bladder gradually applies pressure to the radial artery of the patient.

12. The radial artery compression device of claim 11, wherein the device is configured to apply pressure to the radial artery in a manner that prevents blood from flowing out through an opening in the radial artery to thereby achieve hemostasis at the opening.

13. The radial artery compression device of claim 1, wherein the pressure control mechanism is configured to, once the pressure bladder has been inflated, to reduce the pressure in the pressure bladder to a desired level.

14. The radial artery compression device as in claim 1, further comprising a restrictor disposed between the body and the securing means, the restrictor being formed from a material configured to direct a force from the bladder toward a patient's artery when the bladder is inflated.

15. The radial artery compression device as in claim 1, wherein the pressure bladder is a disk shaped.

16. The radial artery compression device as in any of claim 1, wherein the pressure control mechanism comprises an exhaust valve.

17. The radial artery compression device as in any of claim 1, wherein the pressure control mechanism is manually operable by a user.

* * * * *